United States Patent
Koike et al.

(10) Patent No.: US 6,221,092 B1
(45) Date of Patent: Apr. 24, 2001

(54) CLOSURE DEVICE FOR TRANSCATHETER OPERATIONS AND CATHETER ASSEMBLY THEREFOR

(75) Inventors: Kazuyuki Koike, deceased, late of Tokyo-to, by Noriko Koike, Kanako Koike, Yusuke Koike, legal representatives; Toshiki Kobayashi, Kawagoe; Yoshikazu Kishigami; Katsuya Miyagawa, both of Osaka, all of (JP)

(73) Assignee: Nissho Corporation (JP)

( * ) Notice: Subject to any disclaimer, the term of this patent is extended or adjusted under 35 U.S.C. 154(b) by 0 days.

(21) Appl. No.: 09/280,549

(22) Filed: Mar. 30, 1999

(30) Foreign Application Priority Data

Mar. 30, 1998 (JP) .................................................. 10-083409

(51) Int. Cl.$^7$ .................................................. A61B 17/08
(52) U.S. Cl. ........................................... 606/213; 606/151
(58) Field of Search .................................. 606/213, 215, 606/151

(56) References Cited

U.S. PATENT DOCUMENTS

| 5,108,420 | 4/1992 | Marks . | |
|---|---|---|---|
| 5,350,399 | * 9/1994 | Erlebacher et al. | 606/213 |
| 5,683,411 | 11/1997 | Kavteladze et al. . | |
| 5,861,003 | * 1/1999 | Latson et al. | 606/213 |
| 5,944,738 | * 8/1999 | Amplatz et al. | 606/213 |
| 5,976,174 | * 11/1999 | Ruiz | 606/213 |

FOREIGN PATENT DOCUMENTS

| 4222291C1 | 1/1994 | (DE) . |
|---|---|---|
| 556564A2 | 8/1993 | (EP) . |
| 5237128 | 9/1993 | (JP) . |
| 9313712 | 7/1993 | (WO) . |
| 9741778 | 11/1997 | (WO) . |

* cited by examiner

*Primary Examiner*—Michael H. Thaler
(74) *Attorney, Agent, or Firm*—Birch, Stewart, Kolasch & Birch, LLP (57) ABSTRACT

A closure device for transcatheter operations comprises an easily foldable closure member with a shape-restoring force, an easily inflective fixing member of an elastic material, and an easily inflective elastic member having either ends respectively fixed to the fixing member or closure member and holding the closure member and the fixing member in close proximity to one another. The closure device is used in combination with a catheter assembly comprising an elongated sheath opened at both ends and adapted to accommodate the folded closure device therein, and an operating member having at a distal end thereof a holding element for releasably holding the closure device and for guiding and protruding the folded closure device inserted in the sheath from a distal end of the sheath.

5 Claims, 7 Drawing Sheets

CLOSURE DEVICE FOR TRANSCATHETER OPERATIONS AND CATHETER ASSEMBLY THEREFOR

BACKGROUND OF THE INVENTION

The present invention relates to a closure device and catheter assembly suitable for transcatheter operations, for example, operations for closing or repairing vascular defects or endocardiac defects such as ventricular septal defect.

At the present time, Fontan operations have been used for repair operations of complex cardiac anomalies such as single ventricle. In this operation, a single ventricle is used for the systemic circulation system, and for pulmonary circulation a vein of the systemic circulation system is directly connected to a pulmonary artery, whereby cardiac function is repaired. After this operation, however, a considerable decrease of cardiac output may occur because of increase of a pulmonary vascular resistance or transient ventricular hypofunction. The increase of pulmonary vascular resistance is caused by spasm of the pulmonary circulation system. The considerable decrease of cardiac output occasionally makes it is difficult to perform postoperative management.

In order to avoid the increase of pulmonary vascular resistance and the considerable decrease of cardiac output, it is general practice for the above operation to form a small fenestration or perforation of about 4 mm between atria (most cases, the interatrial septum is made of an artificial membrane), whereby allowing the blood to flow through the small fenestration or perforation. This procedure followed by formation of the small fenestration or perforation is a Fontan fenestration. The surgical operation is mainly carried out as a method of treatment for closure of the small fenestration after Fontan fenestration. However, this surgical operation is followed by thoracotomy of a patient in addition to the treatment of the affected area and thus it is a great burden to a patient. In particular, in case of child patient this burden is considerably large.

Percutaneous transluminal therapeutic catheterization is known as a noninvasive procedure for repairing endocardial defects. In this procedure, closure of atrial septal defect is carried out by transveneously inserting an intercardiac catheter into the heart, and the first clinical success is reported by King and Mill in 1976. In the procedure carried out by King et al, double disk-shaped or umbrella-like members for left and right atria are introduced into the atrium through an insertion tool composed of a double-layered catheter coaxially arranged on a core wire, and then united into one so that an interatrial septum is sandwiched in between the umbrella-like members to occlude the atrial septal defect (ASD). However, this procedure requires use of a very large-sized insertion tool and hard umbrella-like members, thus making it impossible to apply it to children, especially, to preschool children.

To solve this problem, Rashkind investigated miniaturization of the device and developed a plug of a single umbrella type with hooks to close atrial septal defects. A clinical success in child was reported in 1977. However, this procedure has another problem such that hooks of the plug are occasionally caught in an unintended site of the heart. Once the umbrella-like member is opened, the umbrella-like member can not change its position or withdraw from the hooked site, resulting in emergency operation. To overcome the above disadvantages, Rashkind further developed an improved plug comprising united double umbrella-like members. This plug is widely put into clinical use for occlusion of patent ductus arteriosus.

On the other hand, Lock et al developed a clamshell-shaped interatrial closure device by additionally incorporating a coil spring into a middle portion of each of eight stainless frames of the plug of Rashkind, as disclosed in Japanese patent application (Japanese unexamined patent publication No. 5-237128). This closure device is firmly fixed to the thin interatrial septum by closely adhering double umbrella-shaped members to each other in the overlapping state. Because of its configuration similar to the shell of a clam of a bivalve, this device is called the "clamshell-shaped septal occluder". The procedure is carried out by introducing an elongated sheath with a thickness of 11 French into the repair site through the femoral vein. This procedure is applicable to a patient with a weight of more than 8 kg and therefore widely used for closure of atrial septal defects by means of percutaneous transluminal therapeutic transcatheterization.

The closure treatment of the small fenestration after Fontan fenestration is done with the closure device as the percutaneous transluminal therapeutic transcatheterization.

However, if the closure treatment of the small fenestration after Fontan fenestration is performed with the closure device of the prior art, adhesion of thrombus may occur because of a large closure plate and there is a high risk of complications. Further, in cases where the closure device has fallen away or dislodged during operation, it is difficult to withdraw the closure device because of the shape or size of the closure device.

SUMMARY OF THE INVENTION

It is therefore an object of the present invention to provide a closure device for transcatheter operations, that is simple in shape, easy to operate, safe and reliable in closure of fenestration, easy to withdraw and less in adhesion of thrombus.

Another object of the present invention is to provide a catheter assembly for introducing the closure device for transcatheter operations into the repair site of a patient.

These and other objects of the present invention are achieved by providing a closure membrane with an easily inflective fixing means to fasten the closure members to a tissue surrounding a defect aperture together with the closure membrane by sandwiching the tissue from the opposite side of the closure membrane against the defect aperture.

According to the present invention, there is provided a closure device for transcatheter operations, that comprises an easily foldable closure member with a shape-restoring force, an easily inflective fixing member of an elastic material, the fixing member being arranged in approximately parallel to a plane of the closure member for fixing closure member to a tissue surrounding a defect aperture by sandwiching the tissue from the opposite side of the closure member against the defect aperture, and an easily inflective elastic member having either ends respectively fixed to the fixing member and closure member and holding the closure member and the fixing member in close proximity one another.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
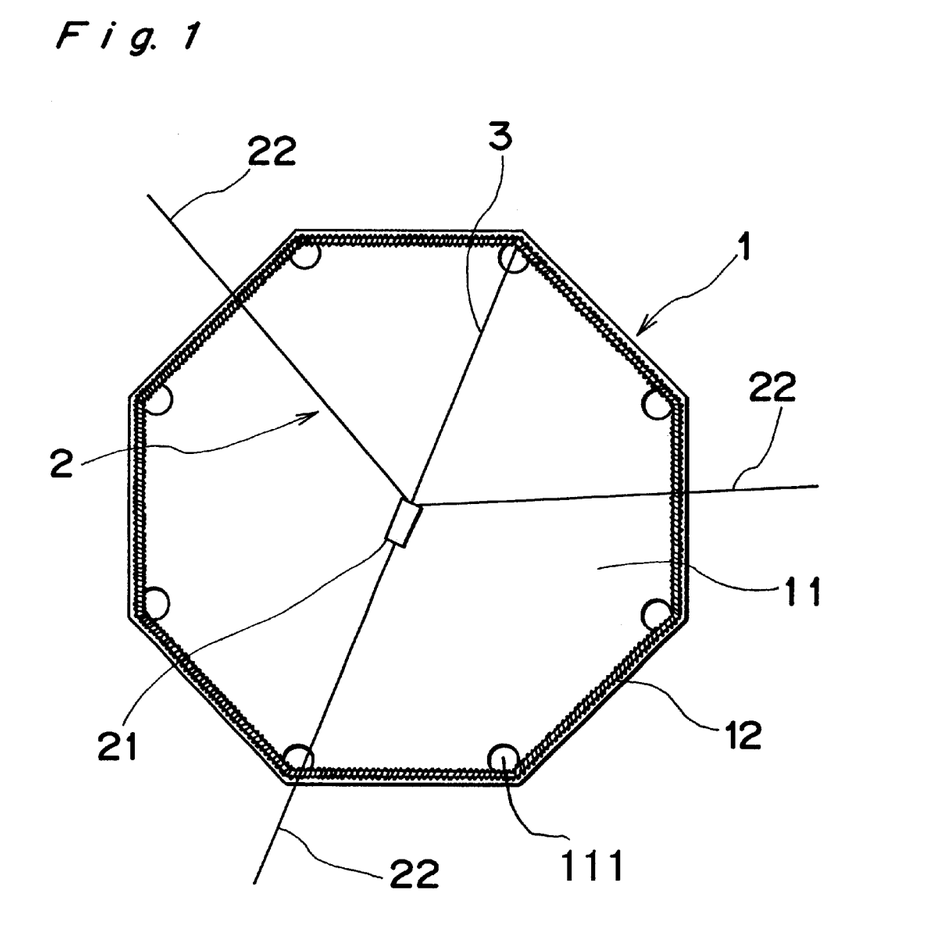
FIG. 1 is a plane view illustrating one embodiment of a closure device according to the present invention.
Figure 2:
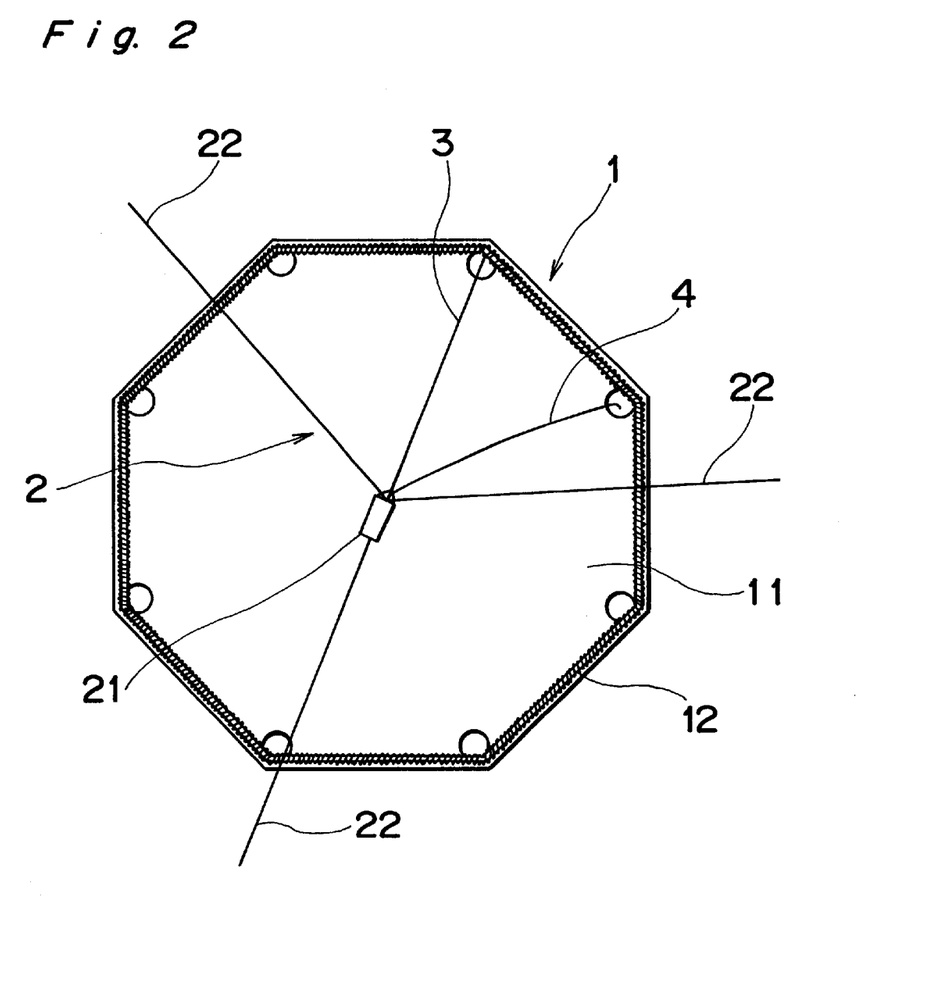
FIG. 2 is a plane view illustrating another embodiment of the closure device according to the present invention.

Referring now to FIGS. 1 and 2, there is shown a closure device C for transcatheter operations according to the present invention. The closure device C includes an easily foldable closure member 1 with a shape-restoring force, a fixing member 2 for fixing the closure member 1 to the tissue surrounding a defect aperture, and an elastic member 3 having either ends respectively fixed to the fixing member 2 and the closure member 1 and holding the closure member and the fixing member in close proximity to one another.

The closure member 1 is preferably composed of a closure membrane 11 of a bio-compatible material and a frame 12 of an elastic material arranged on a peripheral portion of the closure member 1 and sewn thereon with threads. The frame 12 of the closure member 1 may be combined with a base portion 21 of the fixing member 2 with a filament 4 passing through a central portion of the closure membrane 11 of the closure member 1 so that the defect aperture D is located at the central portion of the closure member 1 when the defect aperture D is closed by the closure member 1.

The closure member 1 is an easily foldable and shape-restorable member in the form of a flat sheet, and preferably composed of a closure membrane 11 of fabric or nonwoven fabric made of a bio-compatible material, and an easily inflective frame 12 of an elastic material arranged on a peripheral portion of the closure membrane 11. It is preferred that the closure member 1 has a flat shape in the form of a hexagon or octagon analogous to the shape of the defect aperture D (generally, circle in figure). However, the configuration of the closure member 1 is not limited to these examples. It is sufficient for the closure member 1 to have a size enough to close the defect aperture D. However, it is preferred that the closure member has a size of 1.5 to 2 times larger than that of the defect aperture D.

The bio-compatible material used for the closure membrane 11 may be polyester such as polyethylene terephthalate; polyolephine such as polyethylene, polypropylene; polyamide such as nylon 6, nylon 66; fluoroplastics such as polytetrafluoroethylene, polyvinylidene fluoride; chloride plastics such as polyvinyl chloride, polyvinylidene chloride; polyurethane; semisynthetic plastics such as cellulose acetate, cellulose acetopropionate; and natural fibers. These materials may be used in the form of fabric, nonwoven fabric, film, a porous sheet or a composite of these forms.

The frame 12 is made from an elastic material in linear shape. Preferred elastic materials includes metals such as stainless steels, brasses; flexible plastics such as polyethylene, polypropylene, polyesters and the like; super elastic alloys such as Ni-Ti alloys, Cu-Zn-Al alloys, Cu-Al-Ni alloys and the like. The most preferred elastic material is a super elastic alloy.

The fixing member 2 fixing the closure member 1 to the tissue surrounding the defect aperture D is a member for sandwiching the tissue from the opposite side of the closure member 1 against the defect aperture D. The fixing member 2 is generally composed of 2 to 4 thin threads or filaments 22 combined one another at one end thereof and expaded radially from the combined end or a base portion 21 located at a center of the fixing member 2. The filaments 22 are fixed at their base portion 21 to the elastic member 3 so that they are in parallel to the surface of the closure member 1. The fixing member 2 is made of an easily inflective elastic material similar to that of the frame 12 so that the fixing member can be introduced at the operative site with ease by means of a catheter assembly A mentioned below. The filaments 22 are held in a condition inflected against the base portion 21 during passing through a sheath 5 of a catheter assembly A shown in FIG. 3. After being pushed out from the sheath 5, the filaments 22 return to the expanded state to sandwich the tissue surrounding the defect aperture D from the opposite side of the closure membrane 11 against the defect aperture D.

The elastic member 3 for holding the closure member 1 and fixing member 2 in close proximity to one another is fixed at both ends thereof to the frame 11 of the closure member 1 and the base portion 21 of the fixing member 2. When the elastic member 3 is used in the form of a linear member as shown in FIGS. 1 and 2, the elastic member 3 is arranged in parallel to the plane of the closure member 1 to keep the fixing member 2 approximately parallel to the plane of the closure member 1. The elastic member 3 is made of an easily inflective elastic material similar to those used for the frame 12. Thus, the elastic member 3 is kept in the condition folded in the longitudinal direction of the sheath 5 during passing through the sheath 5 of the catheter assembly A shown in FIG. 3, but returned to an original condition parallel to the plane of the closure member 1 after being pushed out from the sheath 5. At the same time, the fixing member 2 fixed to the elastic member 3 is returned to the condition parallel to the plane of the closure member 1 and sandwich the tissue surrounding the defect aperture D from the opposite side of the closure member 1 against the defect aperture D.

Figure 3:
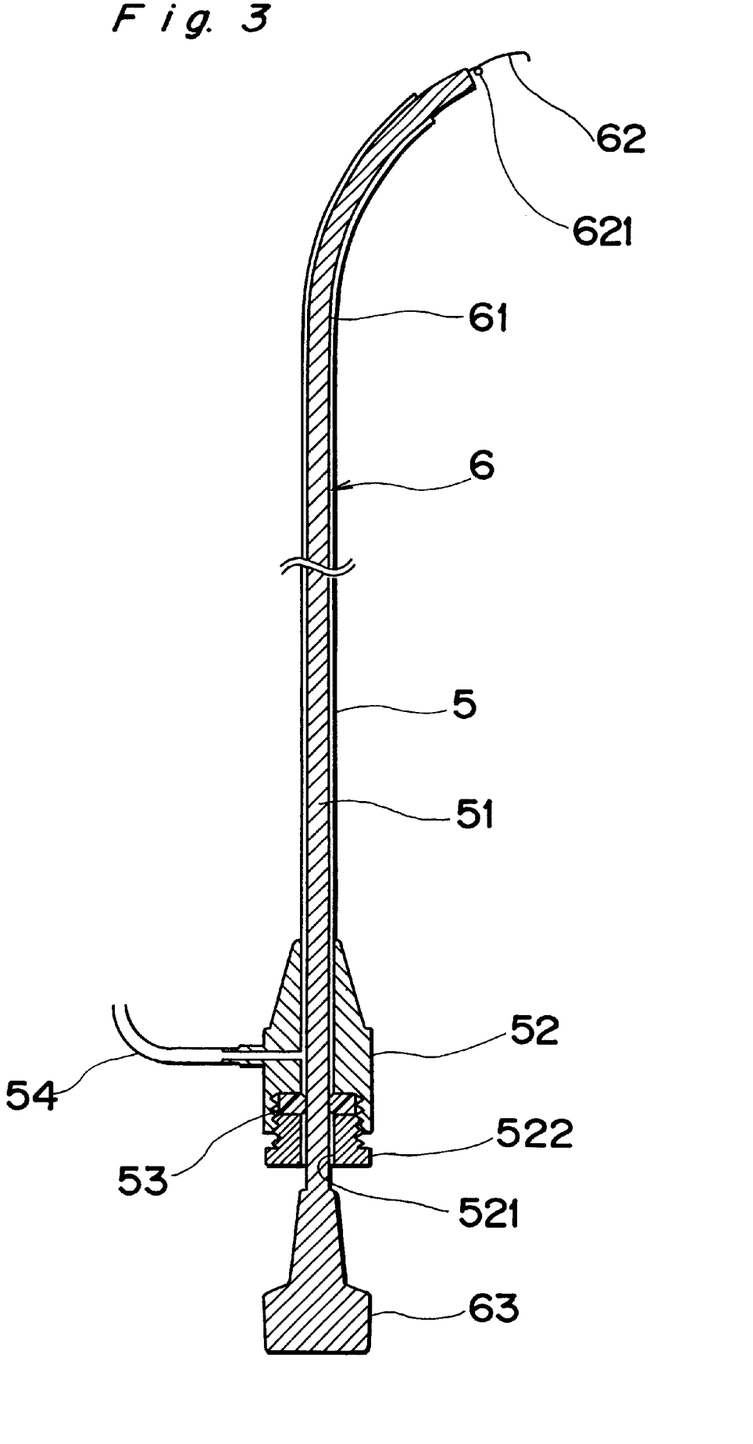
FIG. 3 is a vertical section view of a catheter assembly for use in combination with the closure device of the present invention.

The catheter assembly A according to the present invention comprises a sheath 5, and an operating linear member 6 for introducing the closure device C of the present invention into the operative site through the sheath 5 and for performing the operation of closure of the defect aperture D.

The sheath 5 is a tubular member having a lumen 51 opened at either ends and capable of removably inserting an operating linear member 6 thereinto. The closure device C is inflected and put in the lumen 51 of the sheath 5. The sheath 5 is provided at the proximal end thereof with a connector 52 having an inlet port 521 for the operating linear member 6. The connector 52 is provided with hemostatic means or hemostatic valve to prevent leakage of the blood during operation and a lateral tube 54 for infusion of heparinized physiological saline to prevent blood coagulation during operation. A packing 53 used as the hemostatic means has a through-hole at the central part and is pressed against the lumen of the connector 52 by a screw bolt 522 having a through-hole at the central portion. As a material for the sheath, there may be used those such as fluoroplastics such as polytetrafluoroethylene, synthetic resins such as polypropylene, polyethylene, polyester, polyurethane or the like, and mesh or coiled stainless steels such as SUS 304.

The operating member 6 is provided at a tip of a linear member 61 with a holding means 62 for releasably holding the closure device C and adapted to allow the closure device C to pass through the lumen of the sheath 5 from the proximal end of the sheath 5 to the distal end thereof in the folded condition. Preferably, the holding means 62 may be a flexible linear member extending in the axial direction of the operating member 6. The linear member 61 may be made of a material similar to those used for the sheath 5. As a material for the holding means 62, it is preferred to use an easily inflective elastic material similar to those used for frame 12. The proximal end 621 of the holding means 62 is preferably winded round one time to form a ring portion as shown in FIG. 3 so as to make it easy to be inflected. Since the holding means 62 is made of an elastic material, the holding means 62 can be put in the sheath 5 under the condition inflected to hold the closure device C, and then returned to its original state extending in the axial direction of the operating member 6 to release the closure device when the closure device C is pushed out of the sheath 5. Numeral 63 is a handle for operating the operating member 6.

The use of the catheter assembly A will be explained below, making reference to FIGS. 4–7.

Figure 4:
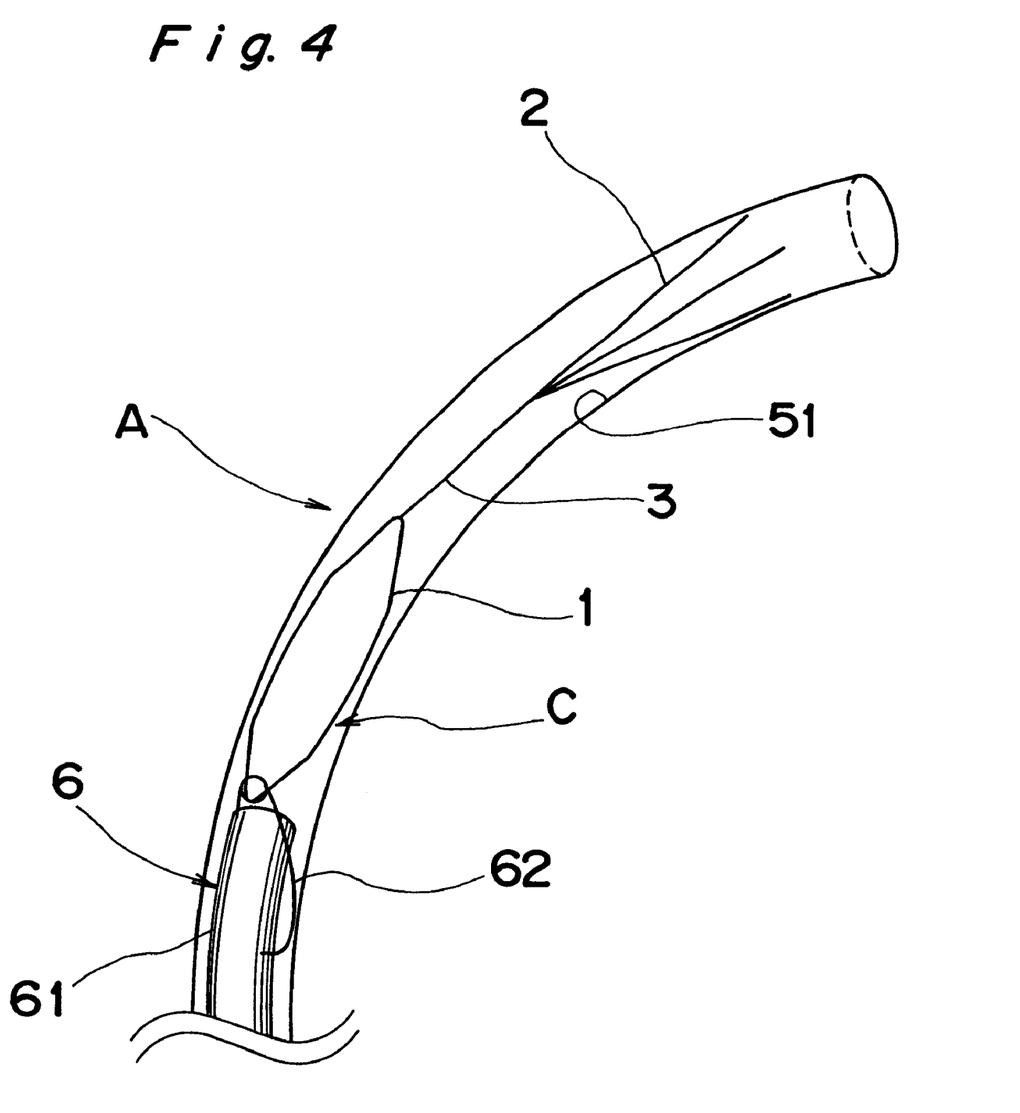
FIG. 4 is a perspective view of the catheter assembly of FIG. 3 with the closure device of FIG. 1 inserted therein.

The tip portion of the holding means 62 of the operating member 6 is passed through a part of the closure membrane 11 adjacent to the frame 12 of the closure device C, or one of holes 111 provided in the membrane 11, half-turned at the ring portion 621 to hold the frame 12 of the closure member C, and then pulled in the sheath 5 of the catheter. Since the holding portion 62 is directed toward the handle 63 and pulled in the sheath 5, the fixing member 2 and elastic member 3 of the closure device 1 are stretched out in the longitudinal direction of the sheath 5 at the opening thereof and pulled in the sheath 5 as shown in FIG. 4.

Figure 5:
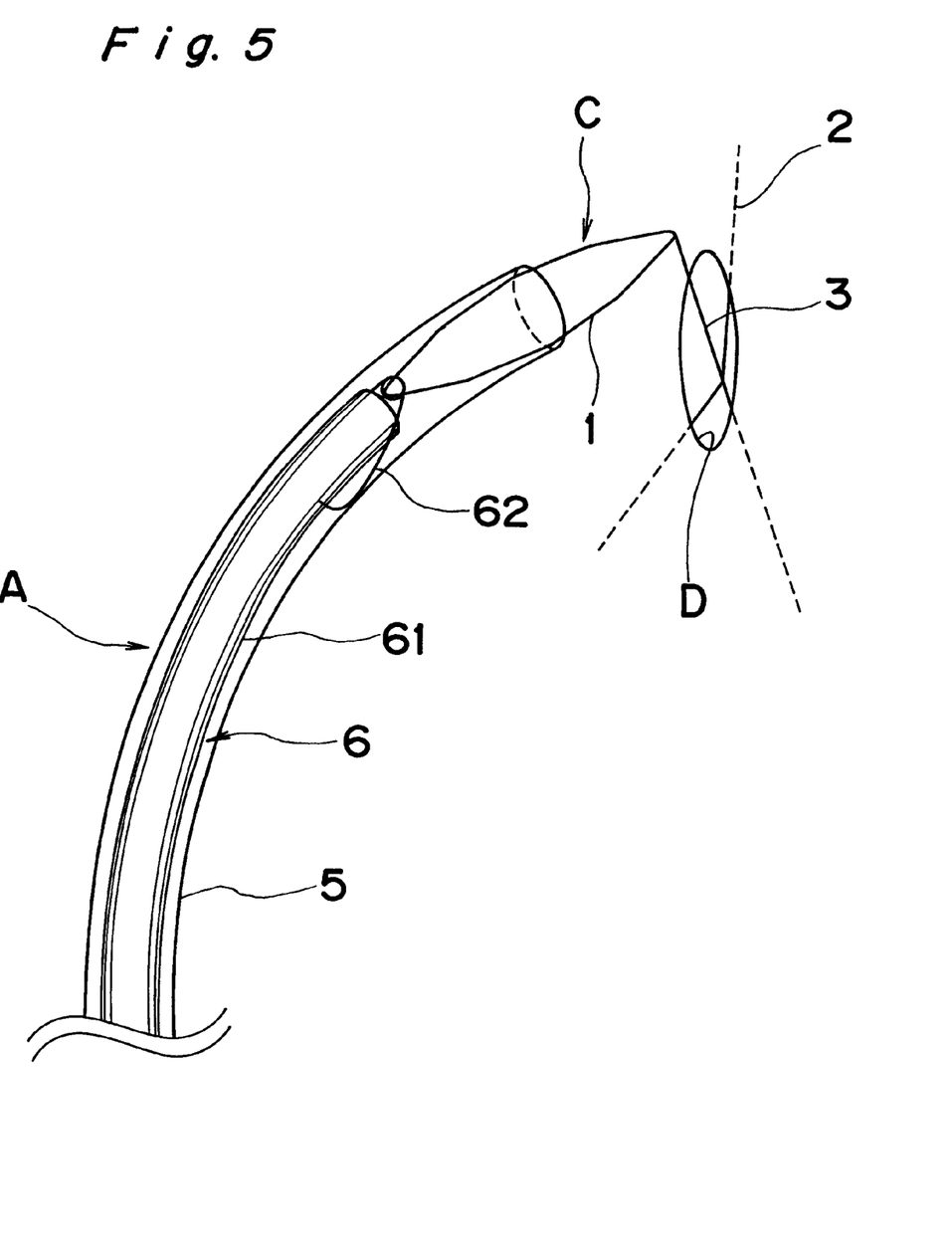
FIGS. 5 to 7 are views illustrating a percutaneous closure treatment employing the closure device and catheter assembly of the present invention.

On the other hand, a long sheath (not illustrated in the figure) is previously introduced into the right atrial of a patient through a femoral vein of the right leg of the patient. The above catheter assembly A is then inserted into the elongated sheath and introduced into the right atrial of a patient through the elongated sheath. The distal end of the catheter assembly A is protruded into the left atrial through the defect aperture D of the atrial septum, and then the fixing member 2 of the closure device C is pushed out of the sheath 5 and into the left atrial by pushing the operating member 6. Simultaneously therewith, the fixing member 2 of the closure device C expands and returns to the original state as shown in FIG. 5, so that the expanded fixing member 2 is unable to pass through the defect aperture D.

Figure 6:
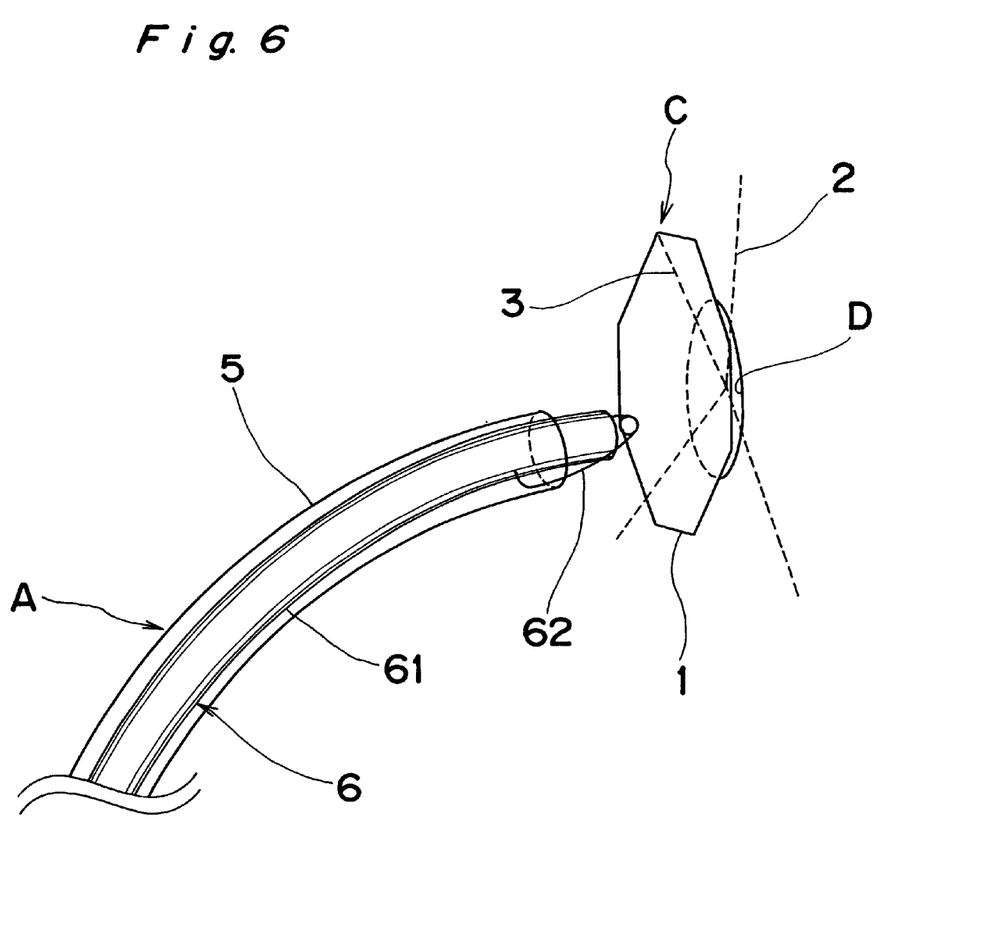
Figure 7:
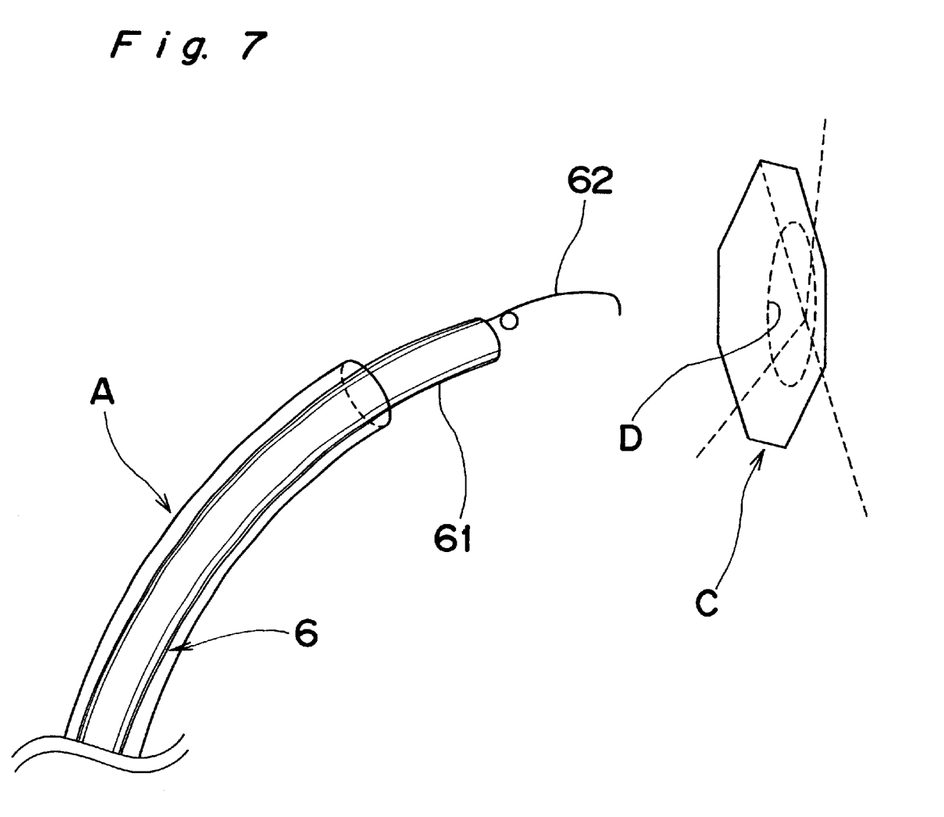

After pulling back the catheter assembly A to the right atrial, the closure member 1 of the closure device C is pushed into the right atrium by pushing the operating member 6, thereby allowing the closure member 1 to expand within the right atrial as shown in FIG. 6. The operating member 6 is further pushed within the sheath 5. If necessary, the sheath 5 may be pulled back during pushing the holding means 62. By pushing the operating member 6, the holding means 62 is pushed out of the sheath 5, whereby allowing the tip portion of the holding means 62 to return to the uninflected state, i.e., the previous state directed in the extended direction of the linear member 61 and then to be disengaged from the closure member C. At the same time, the closure member 1 is returned to its previous unfolded form to sandwich the tissue surrounding the defect aperture D between the closure member and fixing member 2, whereby the defect aperture D is closed and the operation is finished.

As will be understood from the above, a combination of the closure device and catheter assembly according to the present invention makes it possible to easily and infallibly close the defect aperture. Further, it is possible with the closure device of the present invention to solve a problem which occurred during use of the closure device of the prior art, i.e., to minimize the adhesion of thrombus to the closure member. In addition, the present invention makes it possible to easily withdraw the closure device even in cases where the closure device has fallen away or dislodged during operation.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A closure device for transcatheter operations, comprising:
    one sheet of an easily foldable closure member with a shape-restoring force;
    an easily inflective fixing member of an elastic material, the fixing member being composed of radially extending linear filaments and arranged in approximately parallel to a plane of the closure member for fixing the closure member to a tissue surrounding a defect aperture by sandwiching the tissue from the opposite side of the closure member against the defect aperture, the space between said radially extending filaments being unobstructed; and
    an easily inflective elastic member having two ends respectively fixed to the fixing member and closure member to hold them in close proximity to one another.

2. The closure device according to claim 1, wherein the closure member is composed of a closure membrane and an easily inflective frame arranged on a peripheral portion of the closure membrane, the closure membrane being of fabric or nonwoven fabric made of a bio-compatible material, and wherein the frame is made of an elastic material.

3. The closure device according to claim 2, wherein the frame of the closure member is combined with a base portion of the fixing member with a filament passing through a central portion of the closure membrane.

4. A catheter assembly and a closure device for transcatheter operations, the closure device comprising:
    one sheet of an easily foldable closure member with a shape-restoring force;
    an easily inflective fixing member of an elastic material, the fixing member being composed of radially extending linear filaments and arranged in approximately parallel to a plane of the closure member for fixing the closure member to a tissue surrounding a defect aperture by sandwiching the tissue from the opposite side of the closure member against the defect aperture, the space between said radially extending filaments being unobstructed; and
    an easily inflective elastic member having two ends respectively fixed to the fixing member and closure member to hold them in close proximity to one another; and
    wherein the catheter assembly further comprises:
        an elongated sheath opened at both ends and adapted to accommodate the closure device when folded therein, and an operating member having at a distal end thereof holding means for releasably holding the closure device and for guiding and protruding the folded closure device inserted in the sheath from a distal end of the sheath.

5. The catheter assembly according to claim 4, wherein the holding means comprises an easily inflective linear member extending in the axial direction of the operating member.

* * * * *